(12) United States Patent
Crowe et al.

(10) Patent No.: US 12,279,817 B2
(45) Date of Patent: Apr. 22, 2025

(54) PORTABLE SIGHT TESTING APPARATUS

(71) Applicant: 4IZE PTY LTD, New South Wales (AU)

(72) Inventors: Sarah Crowe, New South Wales (AU); Jason Smith, Queensland (AU)

(73) Assignee: 4IZE PTY LTD, New South Wales (AU)

( * ) Notice: Subject to any disclaimer, the term of this patent is extended or adjusted under 35 U.S.C. 154(b) by 497 days.

(21) Appl. No.: 17/783,746

(22) PCT Filed: Dec. 9, 2020

(86) PCT No.: PCT/AU2020/051346
§ 371 (c)(1),
(2) Date: Jun. 9, 2022

(87) PCT Pub. No.: WO2021/113910
PCT Pub. Date: Jun. 17, 2021

(65) Prior Publication Data
US 2023/0008623 A1    Jan. 12, 2023

(30) Foreign Application Priority Data
Dec. 9, 2019  (AU) ................................ 2019904642

(51) Int. Cl.
*A61B 3/00* (2006.01)
*A61B 3/028* (2006.01)
*A61B 3/036* (2006.01)

(52) U.S. Cl.
CPC ............ *A61B 3/0033* (2013.01); *A61B 3/036* (2013.01); *A61B 3/0285* (2013.01); *A61B 2560/0431* (2013.01)

(58) Field of Classification Search
CPC ..... A61B 3/0033; A61B 3/036; A61B 3/0285; A61B 2560/0431
(Continued)

(56) References Cited

U.S. PATENT DOCUMENTS

| | | | |
|---|---|---|---|
| 2004/0032567 A1* | 2/2004 | Fukuma | A61B 3/04 351/228 |
| 2004/0263782 A1* | 12/2004 | Jones | A61B 3/0285 351/215 |

(Continued)

OTHER PUBLICATIONS

International Search Report (English) of the International Searching Authority issued in PCT/AU2020/051346, mailed Feb. 24, 2021; ISA/AU.

*Primary Examiner* — Sharrief I Broome
(74) *Attorney, Agent, or Firm* — Harness, Dickey & Pierce, P.L.C.

(57) ABSTRACT

A portable apparatus for determining refractive error in the human eye comprises an elongate base rail having a left side base rail portion and a right side base rail portion; a first lens carrier housing mounted on the left side base rail portion, a first lens carrier carrying a plurality of corrective lenses and being substantially housed within the first lens carrier housing so as to expose a corrective lens of the first lens carrier in a test position of the first lens carrier housing; a second lens carrier housing mounted on the right side base rail portion, a second lens carrier carrying a plurality of corrective lenses and being substantially housed within the second lens carrier housing so as to expose a corrective lens of the second lens carrier in a test position of the second lens carrier housing; a first user operable control adapted for moving the first lens carrier relative to the first lens carrier housing and a second user operable control adapted to move the second lens carrier relative to the second lens carrier housing, whereby the first user operable control and the second user operable control are each movable to select a corrective lens to be exposed in the test position of the respective carrier housing. and wherein the portable apparatus includes at least one of (a) the base rail is adapted to be foldable at a middle portion thereof and (b) one of the first (Continued)

lens carrier housing and the second lens carrier housing is detachable from the respective left side base rail portion or right side base rail portion.

19 Claims, 14 Drawing Sheets

(58) Field of Classification Search
USPC .......................................................... 351/218
See application file for complete search history.

(56) References Cited

U.S. PATENT DOCUMENTS

| 2006/0244915 | A1* | 11/2006 | Clemons | ................ | A61B 3/032 |
| | | | | | 351/245 |
| 2008/0074619 | A1* | 3/2008 | Gisonna | ............... | A61B 3/0285 |
| | | | | | 351/223 |
| 2014/0176909 | A1* | 6/2014 | Spivey | ..................... | A61B 3/04 |
| | | | | | 351/227 |
| 2017/0027435 | A1* | 2/2017 | Boutinon | ............. | A61B 3/0285 |

* cited by examiner

PORTABLE SIGHT TESTING APPARATUS

CROSS-REFERENCE TO RELATED APPLICATION

This application is a 371 U.S. National Phase of International Application No. PCT/AU2020/051346, filed Dec. 9, 2020, which claims priority to Australian Application No. 2019904642, filed Dec. 9, 2019. The entire disclosures of the above applications are incorporated herein by reference.

TECHNICAL FIELD

The present invention relates to a portable apparatus for determining refractive error in the human eye.

BACKGROUND

Refractive error in the human eye occurs when light cannot accurately focus onto the retina of the eye due to the shape of the eye. Common types of refractive error include near-sightedness, far-sightedness and astigmatism, all of which can be treated with a corrective lens in the form of a contact lens or spectacles. Over one billion people worldwide are visually impaired due to uncorrected refractive error, simply because they do not have access to spectacles. There are three main barriers to the supply of spectacles, particularly in remote and developing communities: lack of professionals to test for glasses, geographic isolation and lack of sight testing equipment, personnel and spectacles, largely due to the cost of providing sight testing and prescription spectacles.

A phoropter is a commonly used piece of sight testing equipment used by opticians to test for refractive error in the human eye. It comprises of cylinders, prisms and lenses that measure the eye's refractive error as well as the eye's natural resting position, binocular vision and eye movements. As such, a phoropter is a complex and fragile piece of equipment that requires skill and training to understand and operate. Furthermore, it is not easily transportable away from its installation site.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

According to an embodiment of the disclosure, a portable apparatus for determining refractive error in the human eye comprises an elongate base rail having a left side base rail portion and a right side base rail portion; a first lens carrier housing mounted on the left side base rail portion, a first lens carrier carrying a plurality of corrective lenses and being substantially housed within the first lens carrier housing so as to expose a corrective lens of the first lens carrier in a test position of the first lens carrier housing; a second lens carrier housing mounted on the right side base rail portion, a second lens carrier carrying a plurality of corrective lenses and being substantially housed within the second lens carrier housing so as to expose a corrective lens of the second lens carrier in a test position of the second lens carrier housing; a first user operable control adapted for moving the first lens carrier relative to the first lens carrier housing and a second user operable control adapted to move the second lens carrier relative to the second lens carrier housing, whereby the first user operable control and the second user operable control are each movable to select a corrective lens to be exposed in the test position of the respective carrier housing, and wherein the portable apparatus includes at least one of (a) the base rail is adapted to be foldable at a middle portion thereof and (b) one of the first lens carrier housing and the second lens carrier housing is detachable from the respective left side base rail portion or right side base rail portion.

The base rail may be adapted to be foldable about a vertical axis so as to fold the portable apparatus in half.

According to some embodiments, one of the first lens carrier housing and the second lens carrier housing is selectively movable on the base rail relative to the other of the first lens carrier housing and the second lens carrier housing to adjust a distance between the first lens carrier housing and the second lens carrier housing According to some embodiments, the first lens carrier and the second lens carrier each comprise a disc, and the plurality of corrective lenses of the respective lens carrier is arranged around a radially outer portion of the disc.

According to some embodiments, the first lens carrier and the second lens carrier are each rotatably mounted within the respective lens carrier housing, and the first user operable control is adapted to rotate the first lens carrier and the second user operable control is adapted to rotate the second lens carrier, to advance a corrective lens of the plurality of corrective lenses into the test position of the respective carrier housing.

In an embodiment, the test position of the first lens carrier housing and the test position of the second lens carrier housing are disposed substantially adjacent one another.

In an embodiment, the base rail includes a hinge disposed between and connecting the left side base rail and the right side base rail, wherein the apparatus is foldable about the hinge.

In an embodiment, the portable apparatus comprises a user operable adjustment mechanism, via which the one of the first lens carrier housing and the second lens carrier housing is selectively translatable on the base rail.

In an embodiment, one of the first lens carrier housing and the second lens carrier housing is slidably mounted on the base rail for adjustable movement of the base rail relative to the one of the first and second lens carrier housings mounted thereon for varying a distance between a test position of the first lens carrier housing and a test position of the second lens carrier housing.

In an embodiment, the base rail includes an indicator of a distance between a centre of a corrective lens in the test position of the first lens carrier housing and a centre of a corrective lens in the test position of the second lens carrier housing.

In an embodiment, the first lens carrier housing and the second lens carrier housing each include a viewing window to an indicator of the lens power of the corrective lens in the test position.

In an embodiment, the portable apparatus further includes an additional lens attachment that is removably attachable to each of the first lens carrier housing and the second lens carrier housing.

In an embodiment, the additional lens attachment includes a magnetic housing adapted for removable attachment to each of the first lens carrier housing and the second lens carrier housing.

In an embodiment, the additional lens attachment includes an astigmatic testing lens. In an embodiment, the additional lens attachment includes a further corrective lens.

In an embodiment, the base rail includes a mounting portion adapted for mounting the portable apparatus on a tripod or stand.

In an embodiment, the mounting portion may comprise a mounting bracket or alternatively the mounting portion may be a part of the hinge.

BRIEF DESCRIPTION OF DRAWINGS

An example of the invention will now be described with reference to the accompanying drawings, in which.

DESCRIPTION OF EMBODIMENTS

Figure 1:
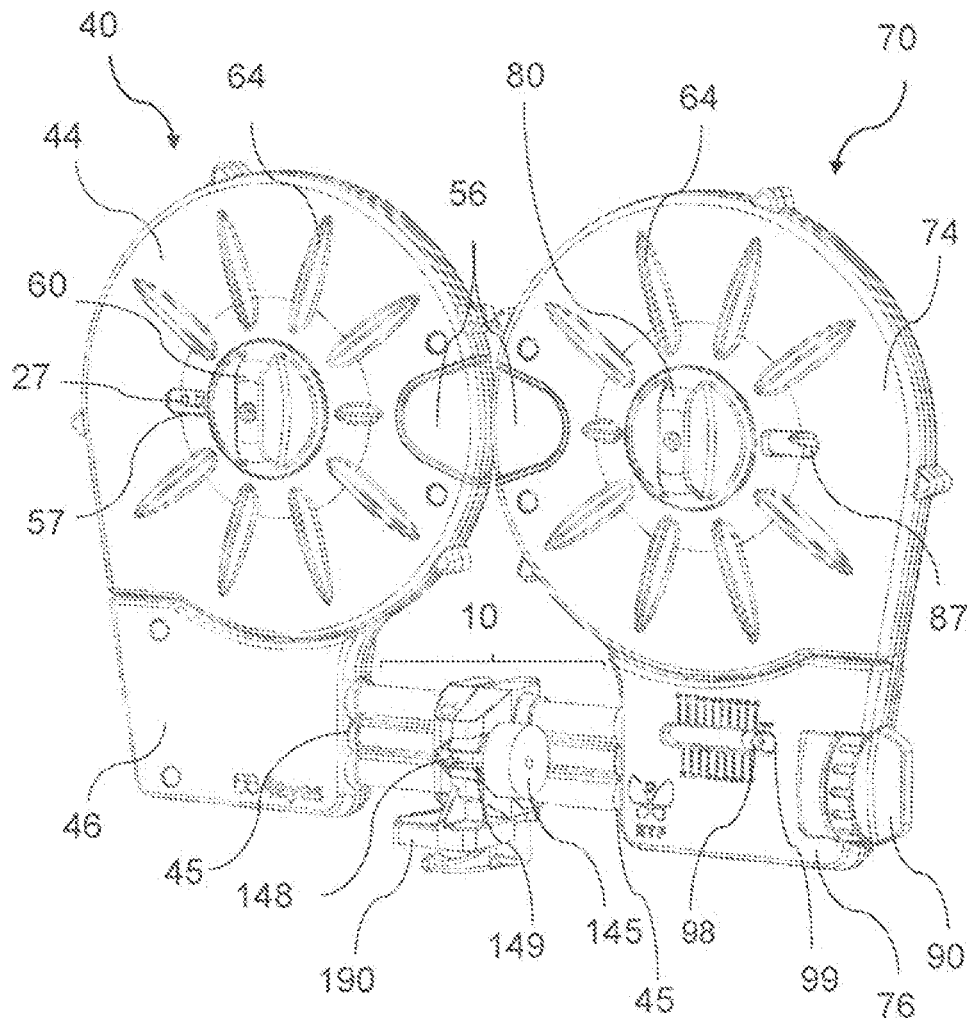
FIG. 1 is a front perspective view of the portable apparatus.

FIGS. 1 to 10 illustrate an embodiment of a portable apparatus 1 for determining refractive error in the human eye. The apparatus 1 includes a base rail 10, a first lens carrier 20 and a second lens carrier 30. The first lens carrier 20 and the second lens carrier 30 are housed in a first lens carrier housing 40 and a second lens carrier housing 70 respectively.

Figure 3:
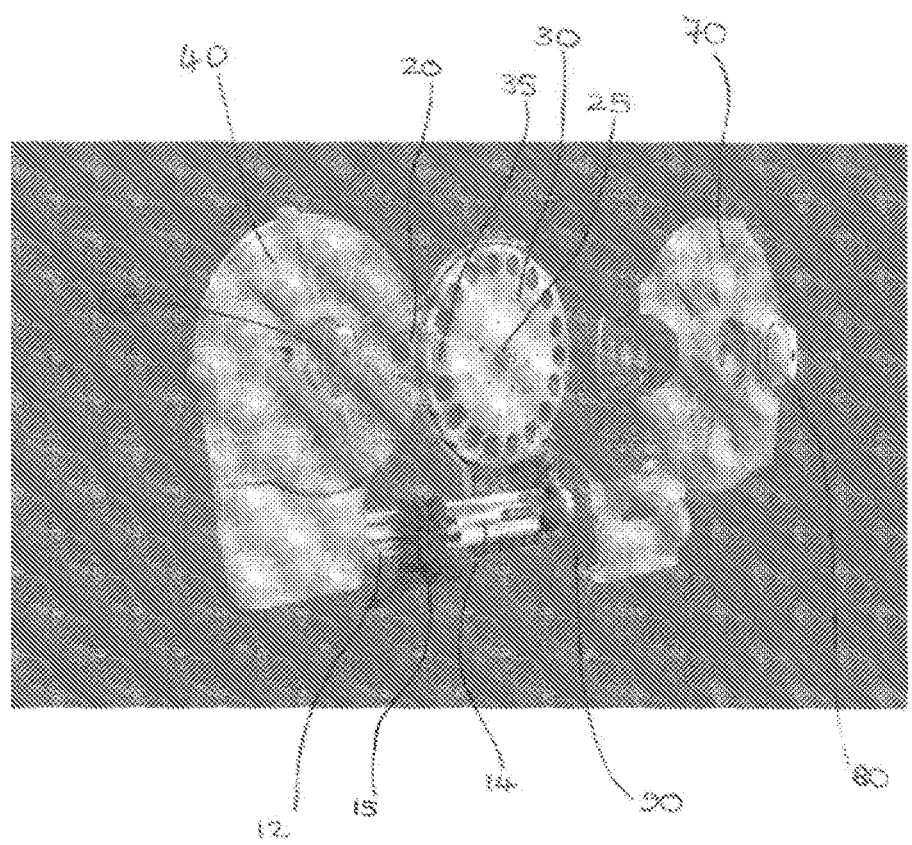
FIG. 3 is a partially exploded front perspective view of the portable apparatus.
Figure 7:
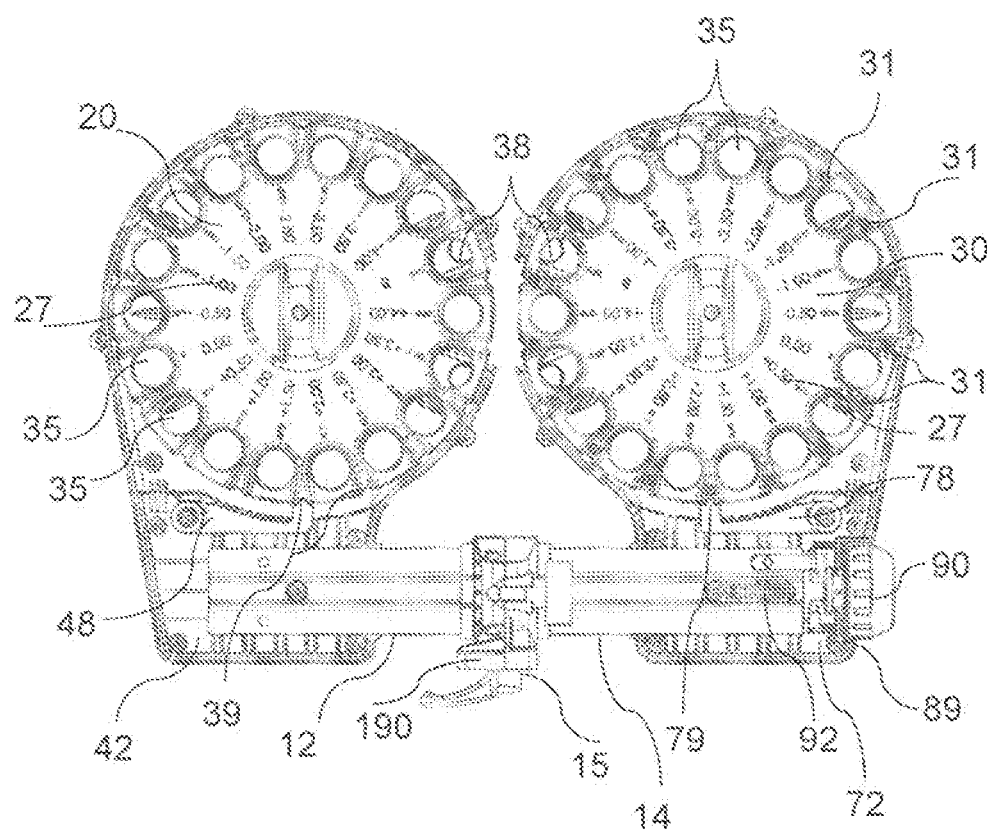
FIG. 7 is a front view of the portable apparatus with the front casings removed for clarity.

The first lens carrier 20 and the second lens carrier 30 are best seen in FIG. 3 and FIG. 7. Each consists of a generally circular plastic disc having a plurality of spherical corrective lenses 35 arranged in the disc around its circumference. In the embodiment shown, the lens carrier 30 carries seventeen spherical corrective lenses 35 ranging in power from −4.00 to +4.00 in increments of 0.5 as well as a blackout lens 38, arranged around a radially outer part of the disc i.e. at its perimeter. The corrective lenses 35 are affixed into circular apertures in the first lens carrier 20 and second lens carrier 30 fastening means such as screws 31 or adhesive. At the centre of the lens carrier 20, 30 is a short hollow cylindrical protrusion 25 (seen in FIG. 3) that functions to locate the lens carrier 20, 30 in position inside the lens housing 40, 70. An indicator 27 of the lens power is printed, etched or otherwise provided on a front face of the disc. A detent notch 39 is provided in the circumference of the disc between each adjacent pair of lenses 35, for use in positioning a corrective lens 35 in a test position 5 of the respective one of the first and second lens carrier housing 40, 70.

The base rail 10 includes a first base rail portion 12 and a second base rail portion 14 that are arranged to extend longitudinally either side of a central hinge 15. The portable apparatus 1 is to a large extent symmetric about the central hinge 15. In use of the apparatus, the first base rail portion 12 is connected to and extends to the left side of the central hinge 15 whilst the second base rail portion 14 is connected to and extends to the right of the central hinge 15. Accordingly, the first base rail portion 12 is also referred to herein as the left side base rail portion and the second base rail is also referred to herein as the right side base rail portion.

The first lens carrier housing 40 comprises of upper and lower rear casings 42, 52 and upper and lower front casings 44, 46. Each of the casings 42, 52 and 44, 46 comprises a hard plastic moulded casing. The upper rear casing 42 is a generally circular shaped plate that is sized to house the first lens carrier 20. The upper rear casing 42 has a shallow upstanding peripheral flange 41 that is adapted both for receiving the lens carrier 20 therein and for carrying a plurality of spaced fixing tabs 43 for fixing the upper rear casing 42 to the upper front casing 44. The upper rear casing 42 also has a central protrusion (not seen) upon which the first lens carrier 20 is received to locate the lens carrier 20 on the upper rear casing 42. The lower front casing 52 has a generally rectangular trapezoidal shape and also has a peripheral flange 58. The peripheral flange 58 is adapted for being mounted onto the left side base rail portion 12. The lower rear casing 52 includes several integrally moulded ribs for supporting the left side base rail portion 12 therein and further includes a plurality of integrally moulded fixture housings 47 for receiving fastening members such as screws 62 (seen in FIG. 7) therein. A spring loaded ratchet arm 48, seen in FIG. 7, is attached to a front of the lower rear casing 42. The ratchet arm 48 extends generally parallel with the base rail 12 and includes a right angled portion at a distal end thereof that projects upwardly toward the first lens carrier 20 in use. The ratchet arm 48 has a semi-circular tip 49 that engages the detent notch 39 of the first lens carrier 20. The ratchet arm 48 is biased upwardly such that the tip 49 engages whichever of the detent notches 39 is present at the bottom of the first lens carrier 20 as it is user rotated via the control knob 60.

Figure 4:
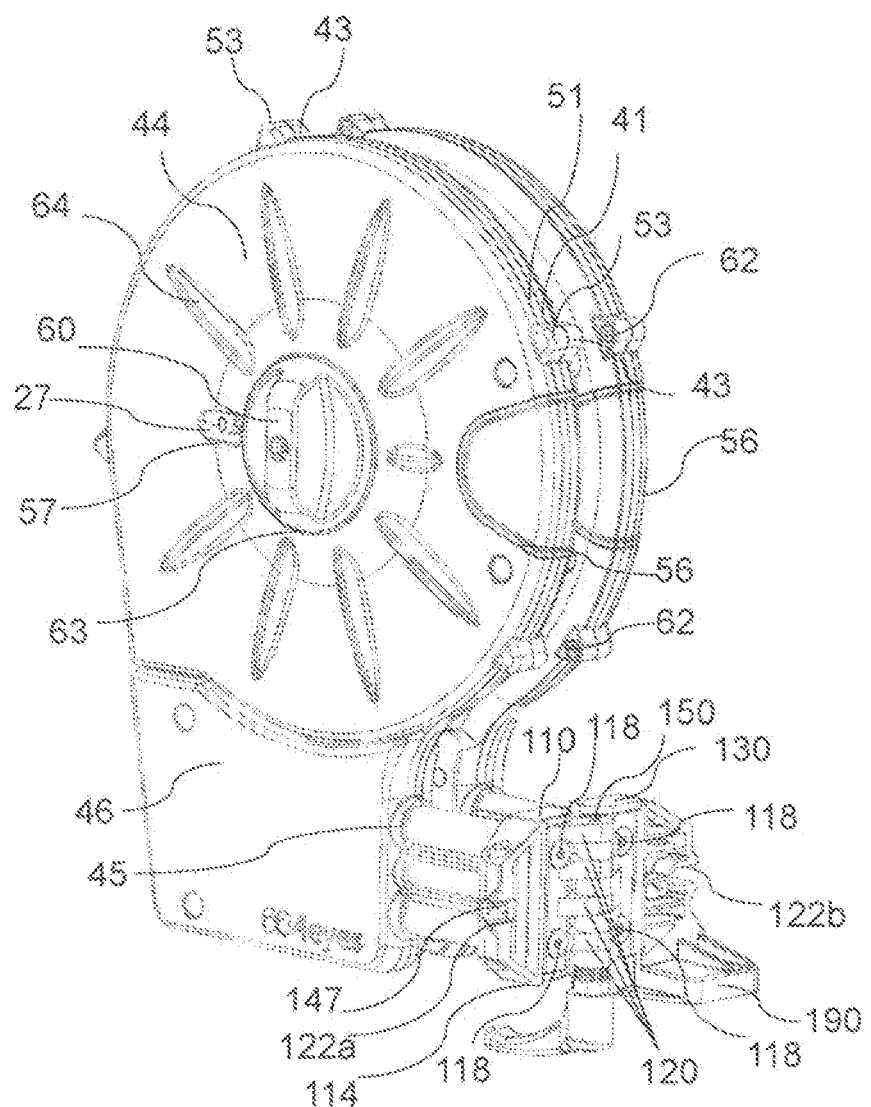
FIG. 4 is a front perspective view of the portable apparatus in a folded configuration.

The upper front casing 44 of the first lens carrier housing 40, best seen in the exploded view of FIG. 3 and in FIG. 4, comprises a generally circular moulded plate having a central aperture 61 and a circular flange 63 surrounding the central aperture 61 and defining a central recess around the central aperture 61. A plurality of radial support ribs 64 are moulded into the casing 44 to provide rigidity and strength. The central recess houses a control knob 60, as described later. A peripheral rim 51 extends around the upper front plate 44 and includes a plurality of spaced fixing tabs 53 that correspond in location to the fixing tabs 43 of the upper rear casing 42. The fixing tabs 53 include housings to receive fixing screws 62 therein to attach the upper front casing 44 to the upper rear casing 42. The upper front casing 44 includes a cut-out segment 5 at a "3 O'clock" position of the circular plate. The cut-out segment 5 in the casing 44 defines a test position of the first lens carrier housing 40. The cut-out segment 5 exposes a corrective lens 35 of the first lens carrier 20 in the test position, seen in FIG. 3 and FIG. 9. A removable transparent cover 56 clips onto the cut-out segment 5 to complete the disc shape and to protect the corrective lens 35 and the first lens carrier 20 when the portable apparatus 1 is not in use. The upper front casing 44 includes an aperture 57 that provides viewing access to the indicator of lens power 27 on the front face of the first lens carrier 20.

Figure 2:
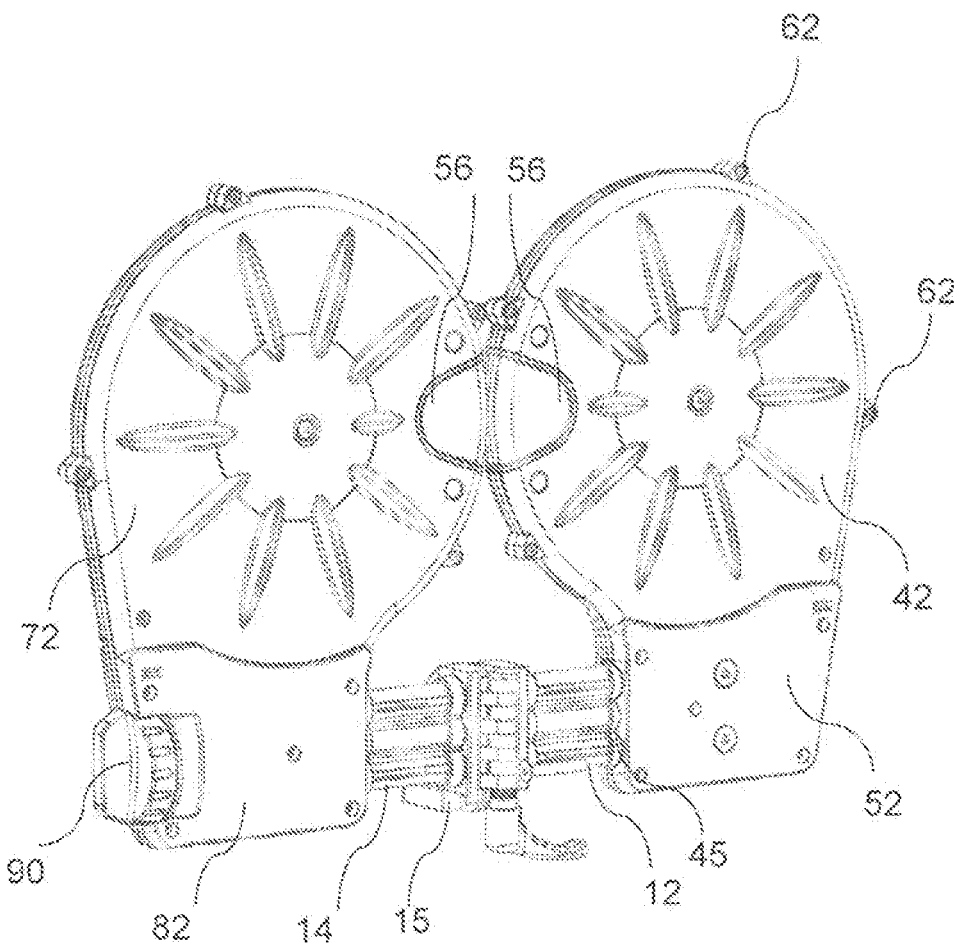
FIG. 2 is a rear perspective view of the portable apparatus.

The lower front casing 46 is a moulded plastic plate that has a generally rectangular trapezoidal shape that corresponds to the shape of the lower rear casing 52. The lower front casing 46 has a partially concave upper edge that corresponds to the curvature of the upper front casing 44. The lower front casing 46 has a peripheral rim 55 that corresponds with the peripheral flange 58 of the lower rear casing 58 so that the two meet as the front casing 46 is assembled onto the lower rear casing 52. The front casing 46 includes a plurality of integrally moulded fixing housings corresponding in location to the fixing housings 47 of the upper rear casing 42. Screws 62, seen in FIG. 2, FIG. 4 and FIG. 5 are used to fasten the upper rear casing 42 to the lower front casing 46 to assemble the apparatus 1.

The second lens carrier housing 70 is essentially a mirror image of the first lens carrier housing 40 and comprises of two hard plastic upper and lower rear casings 72,82 and two hard plastic front casings 74, 76. The upper rear casing 72 is a generally circular shaped plate that is sized to house the second lens carrier 30. The upper rear casing 72 has a shallow upstanding peripheral flange 71 that is adapted both for receiving the lens carrier 30 therein and for carrying a plurality of spaced fixing tabs 73 for fixing the upper rear casing 72 to the upper front casing 74. The upper rear casing 42 also has a central protrusion (not seen) upon which the second lens carrier 20 is received to locate the lens carrier 30 on the upper rear casing 72. The lower front casing 76 has a generally rectangular trapezoidal shape and also has a peripheral flange 88. The peripheral flange 88 is adapted for being mounted onto the right side base rail portion 14. The lower rear casing 82 includes several integrally moulded ribs for supporting the right side base rail portion 14 therein and further includes a plurality of integrally moulded fixture housings 77 for receiving fastening members such as screws 62 (seen in FIG. 2 and FIG. 7) therein. A spring loaded ratchet arm 78 is attached to a front of the lower rear casing 82. The ratchet arm 78 extends generally parallel with the base rail portion 14 and includes a right angled portion at a distal end thereof that projects toward the second lens carrier 30 in use. The ratchet arm 78 has a semi-circular tip 79. The ratchet arm 78 is biased upwardly towards the second lens carrier 30 such that the tip 79 engages whichever detent notch 39 is present at the bottom of the second lens carrier 30.

The lower rear casing 82 differs from the lower rear casing 52 in that it is adapted for accommodating an adjustment mechanism for adjusting a width of the apparatus. Accordingly, the lower rear casing 82 includes a generally rectangular recess 84 in an outer-most part of the lower rear casing 82. The recess 84 and surrounding support structure is adapted for receiving an adjustment knob 90 therein as will be described later.

Figure 5:
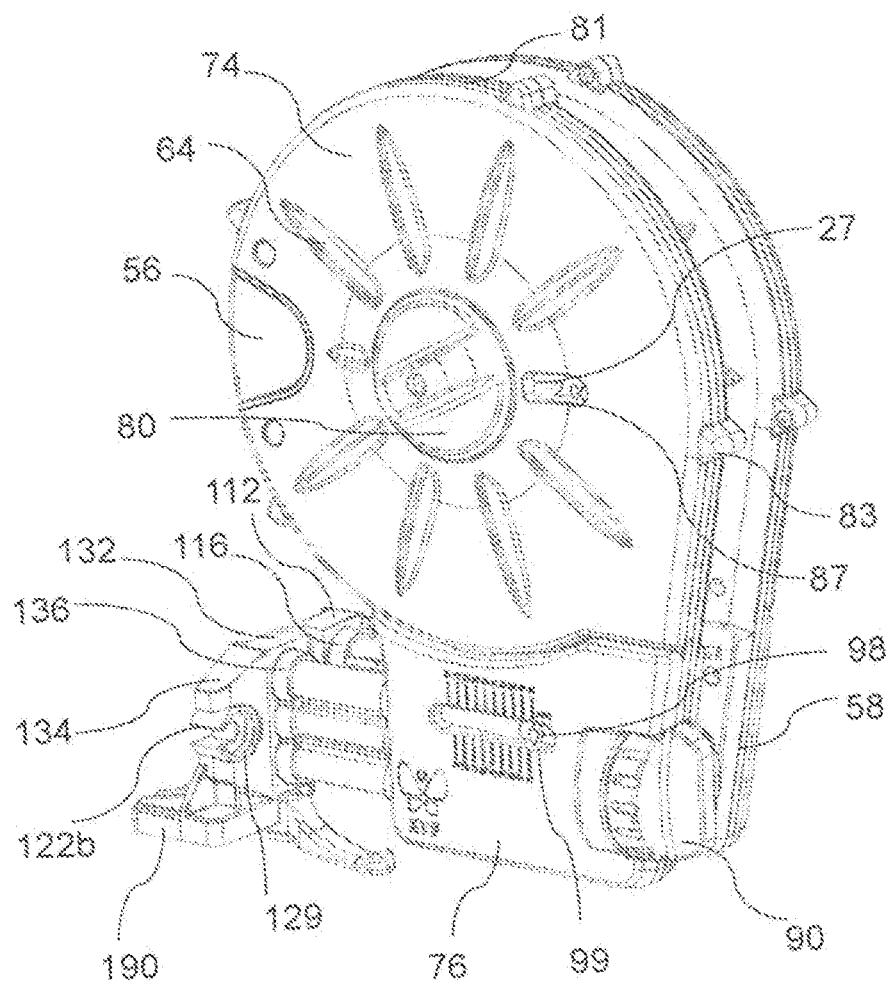
FIG. 5 is a rear perspective view of the portable apparatus in a folded configuration.
Figure 6:
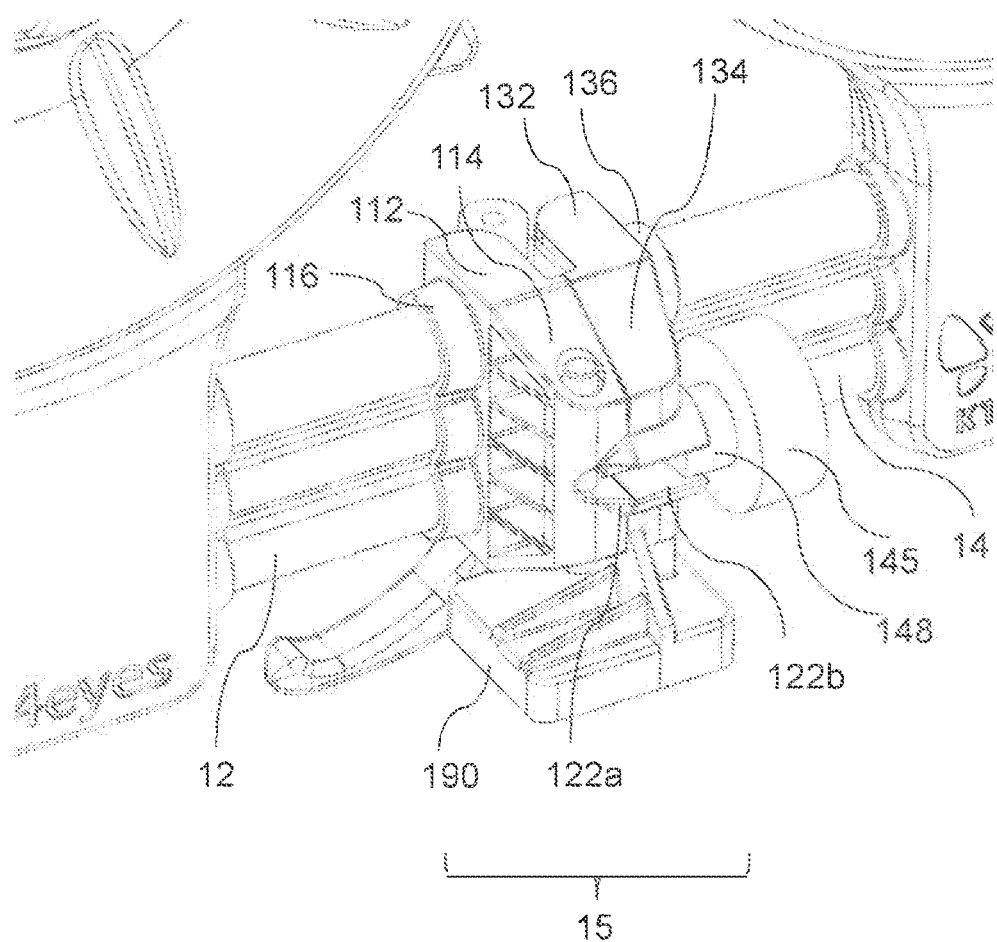
FIG. 6 is a close-up view of the central hinge in an open configuration of the portable apparatus.

The upper front casing 74 of the second lens carrier housing 70, best seen in FIG. 1, FIG. 5 and in the exploded view of FIG. 3, comprises a generally circular moulded plate having a central aperture 61 and a circular flange 63 defining a central recess around the central aperture 61. A plurality of radial support ribs 64 are moulded into the casing 74 to provide rigidity and strength. The central recess 63 houses a user operable control knob 80, which is attached to the central protrusion 25 for user rotation of the second lens carrier 30. A peripheral rim 81 extends around the upper front plate 74 and includes a plurality of spaced fixing tabs 83 that correspond in location to the fixing tabs 73 of the upper rear casing 72. The fixing tabs 83 include housings to receive fixing screws 62 therein to attach the upper front casing 74 to the upper rear casing 72. The upper front casing 74 includes a cut-out segment 7 at a "9 O'clock" position of the circular plate. The cut-out segment 7 in the casing 74 defines a test position of the second lens carrier housing 70. The cut-out segment 7 exposes a corrective lens 35 of the second lens carrier 30 in the test position. A removable transparent cover 56 clips into the cut-out to complete the disc shape and to protect the corrective lens 35 and the second lens carrier 30 when the portable apparatus 1 is not in use. The upper front casing 74 includes an aperture 87 that provides viewing access to the indicator of lens power 27 on the front face of the second lens carrier 20.

The lower front casing 76 has a generally rectangular trapezoidal shape with a partially concave upper edge that corresponds to the curvature of the upper front casing 74. The lower front casing 76 has a peripheral rim 85 that corresponds with the peripheral flange 71 of the lower rectangular portion of the upper rear casing 72 so that the two meet as the front casing 76 is assembled onto the upper rear casing 72. The front casing 76 includes a plurality of integrally moulded fixing housings corresponding in location to the fixing housings 77 of the upper rear casing 72. The screws 62, seen in FIG. 2 are used to fasten the lower rear casing 82 to the lower front casing 76 to assemble the apparatus 1. The lower front casing 76 further includes a rectangular recess 89 and adjacent supporting structure for accommodating the user operable adjustment knob 90 therein, as will be described later.

The left side base rail portion 12 and right side base rail portion 14 each consist of an elongate section of aluminium extrusion having a ridged or contoured profile for robustness and strength. The ridges/contours also provide points of location for the rectangular portions of the upper rear casings 42,72 on the respective portion 12, 14 of the base rail 10. The flanges 45 (seen in FIGS. 1 to 4) of the lower front casings 46, 76 and the lower rear casings 52, 82 are moulded to include contours in the vertical sides thereof that correspond to the ridges in the base rails 12, 14 such that the base rails 12, 14 can be received in a cavity between the lower rear casings 46,76 with a positive location fit. Accordingly, the base rail portions 12, 14 are prevented from moving vertically within the lower front casings 46, 76 and the lower rear casings 52, 82.

As shown in FIGS. 1-7 and 10, the left side base rail portion 12 and the right side base rail portion 14 are connected by the central hinge 15. The central hinge 15 is a hard plastic component comprising a left side hinge component 110 and a right side hinge component 130.

The left side hinge component 110 is attached to a centre-most end of the left side base rail portion 12 and includes a body 112 from which extends a lock portion 114 and a connection flange 116. The body 112 has a height that extends just beyond the height of the base rail portion 12. The connection flange 116, seen in FIG. 5, protrudes laterally from a left side of the body 112. The connection flange 116 is contoured to receive an end of the base rail portion 12 therein with a close fit. The hinge body 112 is fastened to the base rail portion 12 via screws 118 that screw into a side of the body 112 and into an inner end of the base rail portion 12. The front of the body 112 includes a plurality of hinge projections 120 that are spaced vertically along the body and which project rearwardly from a right side of the hinge body 112 at a 45 degree angle thereto. Each of the hinge projections 120 includes an aperture extending vertically there through for receiving a hinge pin 150 therein. The lock portion 114 of the left side hinge component projects laterally from the hinge body 112 and includes a first part 122a of a two-part locking pin housing 122b formed therein.

The right side hinge component 130 is attached to a centre-most end of the right side base rail portion 14 and also includes a body 132 from which extends a lock portion 134 and a connection flange 136. The body 132 has a height that extends just beyond the height of the base rail portion 14. The connection flange 136 protrudes therefrom. The connection flange 136 is contoured to receive an end of the base rail portion 14 therein with a close fit. The hinge body 132 is fastened to the base rail portion 14 via screws 118 that screw into a side of the body 132 and into an inner end of the base rail portion 14. The left side of the body 132 includes a plurality of hinge projections 140 that are spaced vertically along the body 132 at a 45 degree angle thereto, positioned to slot between the hinge projections 120 of the left side hinge component 110. Each of the hinge projections 140 includes an aperture extending vertically there through for receiving the hinge pin 150 therein. The hinge pin 150 is an elongate metal pin that passes through each of the hinge projections 120, 140 to pivotably attach the left side hinge component 110 to the right side hinge component 130. The lock portion of the right side hinge component 130 projects laterally from the body 132 and includes a second part 122b of the two-part locking pin housing 122a, 122b formed therein. The locking pin housings 122a, 122b are configured to receive a magnetic locking pin 145 therein when the apparatus 1 is in an open i.e. unfolded configuration. In this unfolded configuration, the locking portions 114, 134 of the hinge mechanism are disposed adjacent one another such that the two-part locking pin housings 122a, 122b are disposed adjacent one another. In particular, the first locking pin housing 122a is an open fronted horizontal channel having a small hemispherical detent 147 formed in an end thereof that is furthest from the second part of the two-part locking pin housing. The hemispherical detent 147 is formed in a ferromagnetic piece of material that is embedded inside the lock portion 114. In the unfolded configuration of the apparatus 1, the second part 122b of the two-part locking pin housing 122a, 122b is effectively a continuation of the open fronted horizontal channel having a recessed portion 129 the opposite end thereof, the recessed portion 129 having an internal diameter that is larger than the diameter of the open fronted channel.

The magnetic locking pin 145 has a head for user manipulation of the locking pin and a separate main shaft 148 having a diameter sized such that it can be moved in and out of the open fronted channel 122a, 122b. A portion of the main shaft 148 closest to the head is threaded, whilst the opposite end includes a hemi-spherical tip (not seen) sized to fit into and magnetically engage the hemispherical detent 147 in the first part 122a of the locking pin housing 122a, 122b. The shaft 148 is magnetic and the hemispherical tip magnetically attaches to the ferromagnetic hemispherical detent 147. The head 145 is circular and has a diameter and thickness sized for ease of user manipulation. The head 145 also has a hollow shaft portion 149 that is threaded at an interior surface thereof for threaded engagement with the main shaft 148. An exterior diameter of the hollow shaft 149 is sized to be received in the recessed portion of the open fronted channel 122a, 122b. A length of the locking pin 145 is adjustable by turning the locking pin head 145 to screw the hollow shaft 149 further onto the main shaft 148, thereby shortening the locking pin 145. Conversely, unscrewing the head 145 away from the main shaft 148 will increase the length of the locking pin 145. The locking pin 145 is operated as follows. With the apparatus in the folded position as seen in FIG. 4 and FIG. 5, the locking pin 145 resides in the first locking pin housing 122a of the left side hinge component 110, the head 145 protruding from the open fronted channel 122a, 122b. When it is desired to fold the apparatus 1, the left side hinge component 110 and the right side hinge component 130 are brought together by hand. The locking pin 145 can be pivoted out of the open fronted channel 122a, 122b whilst retaining contact with the hemispherical detent 147 so that the head 145 does not obstruct the folding of the apparatus 1. Once the central hinge is in the folded configuration, the locking pin 145 can be pivoted back into the open fronted channel 122a, 122b, such that the head of the locking pin 145, including the hollow shaft 148, lies outside of the open fronted channel 122a, 122b adjacent the right side locking portion 134. The head 145 is then user rotated to screw the hollow shaft 149 onto the main shaft 148 of the locking pin 145. As the head 145 moves toward the locking portion 134, the hollow shaft 149 engages inside the recessed portion 129. In this position of the locking pin 145, as the hollow shaft portion 149 has a diameter that is larger than the opening of the open fronted channel 122a, 122b, the locking pin 145 is prevented from being moved out of the open fronted channel 122a, 122b and the hinge mechanism is locked in the open configuration. When it is desired to unlock the central hinge 15 to fold the apparatus 1, the head 145 of the locking pin is unscrewed out of the locking portion 134 and the locking pin can be pivoted out of the open fronted channel 122a, 122b to allow the opening of the hinge 15 and thereby the folding of the portable apparatus 1.

The right side base rail portion 14 includes an adjusting mechanism for adjusting the width of the apparatus 1 as will now be described. The adjustment mechanism comprises the adjustment knob 90, which is disposed perpendicularly to a longitudinal extent of the base rail portion 14. The adjustment knob 90 has a user operable circular plastic head and a shank 92, a distal part of which is threaded. A horizontal channel 91 is formed in an outer end of the base rail portion 14 to receive the threaded part of the shank 92 therein. A metal endplate 96 is fitted over the outer end of the base rail portion 14. The end plate 96 includes a threaded nut 93 that is coaxial with the horizontal channel 91. The adjustment knob 90 includes a pair of circular flanges 94, 95 that protrude laterally from a proximal portion of the shank 92. The flanges 94, 95 define a shallow recess between them such that when the shank 92 is inserted into the nut 93, the flange 94 abuts the nut 93. The flanges 94, 95 are positioned either side of an outer edge of the lower rear casing 82 and the lower front casing 76 of the second lens carrier housing 70, such that the adjustment knob 90 and the flange 95 are disposed outside of the lens carrier housing 70 and the flange 94 is disposed inside the lens carrier housing 70. With this construction, the recessed portion and shank 92 of the adjustment knob 90 are held captive between the lower front casing 76 and the lower rear casing 82. The adjustment knob 90 is rotatable by a user to screw the shank 92 into or away from the nut 93, thereby changing an offset between the shank 92 and the right side base rail portion 14. The adjustment knob 90 and therefore the shank 92 is fixed in position relative to the second lens carrier housing 70, therefore changing the offset between the shank 92 and the base rail portion 14 moves the right side base rail portion 14 either towards or away from the left side base rail portion 12, varying the width of the apparatus and, more importantly, the distance between the first lens carrier housing 40 and the second lens carrier housing 70. It will be appreciated by the skilled person that whilst the adjusting mechanism is described as being included in/on the right side base rail portion 14 in the embodiment described above and shown in the Figures, that it may equally be included on the left side base rail portion 12 in a different embodiment.

Figure 8:
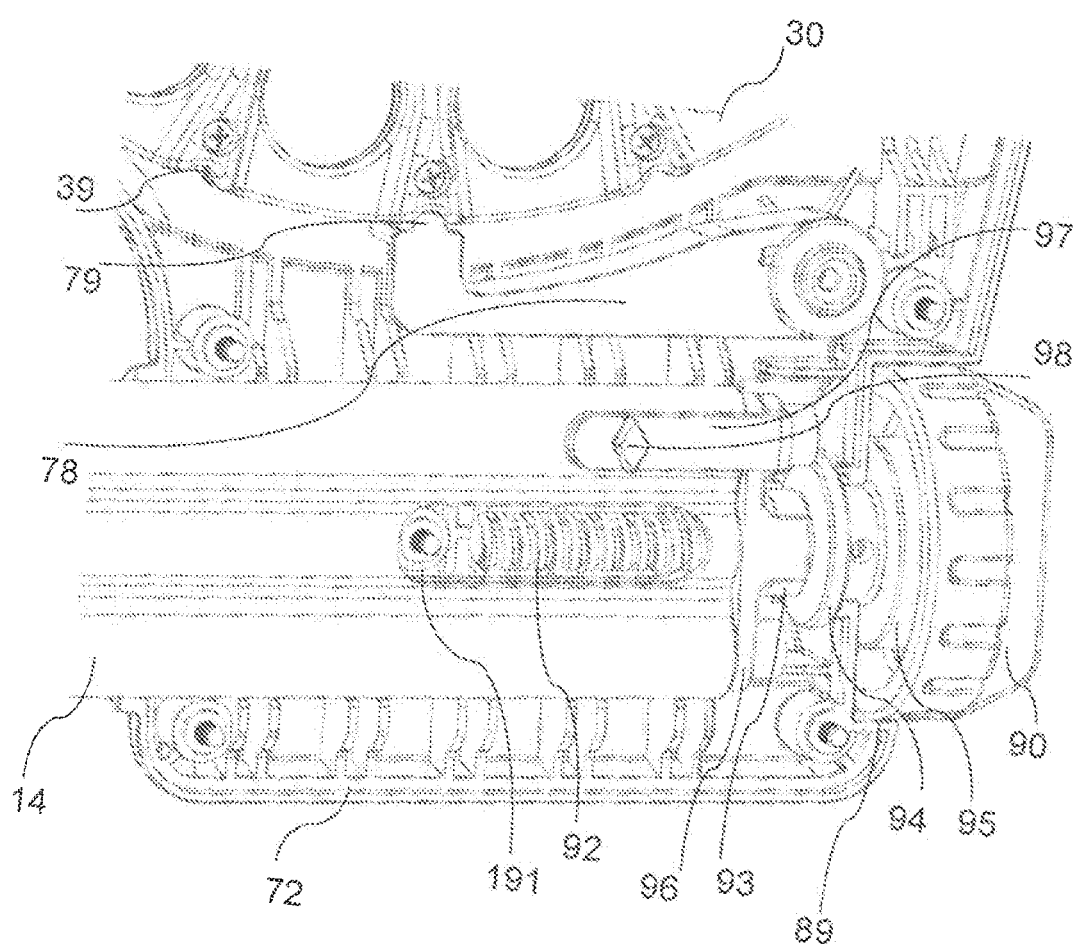
FIG. 8 is a close up of the front perspective view of the portable apparatus of FIG. 7 showing an adjustment mechanism.
Figure 9:
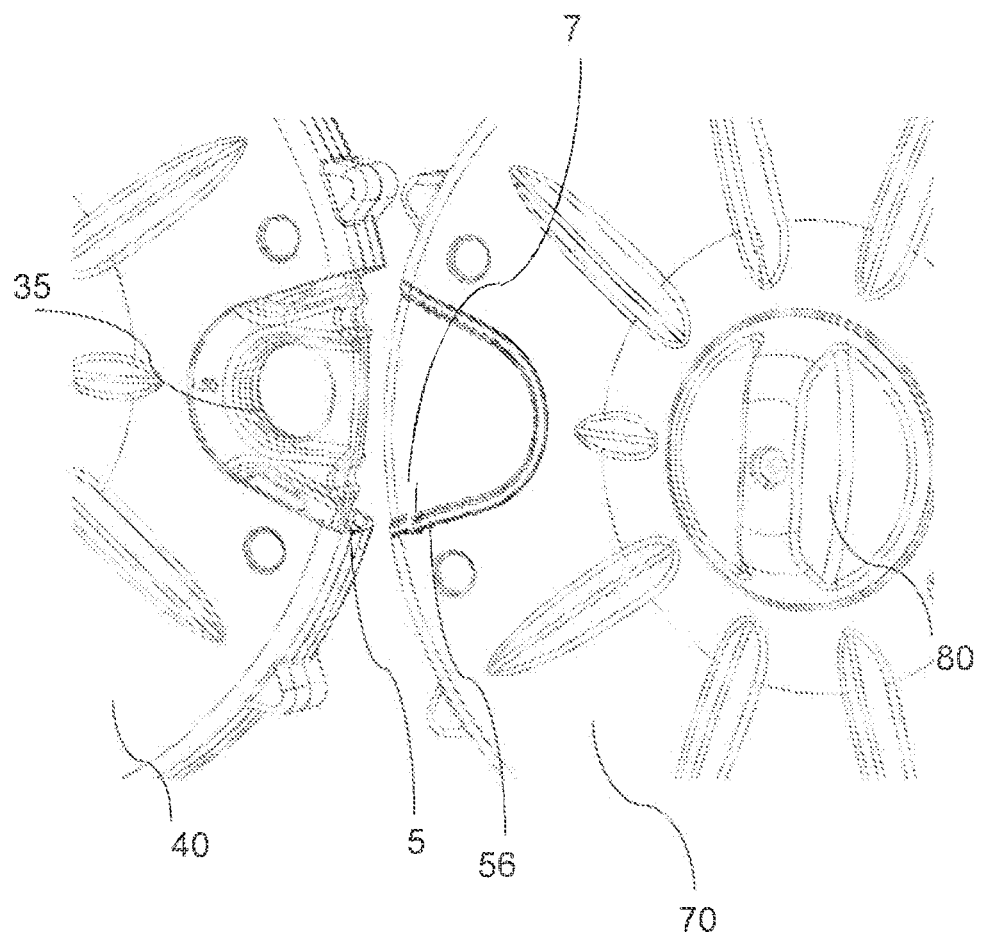
FIG. 9 is a close up front perspective view of the first lens carrier housing and the second lens carrier housing of the portable apparatus with a transparent cover removed for clarity.

As seen in FIG. 7 and FIG. 8, an indicator tab 97 is attached to the end plate 96 and extends longitudinally along the base rail 14 above and in parallel with the shank 92. The indicator tab 97 includes an indicator 98 that marks a position of the base rail portion 14. As seen in FIG. 1 and FIG. 5, the lower front casing 76 has an elongate horizontal aperture 99 in which the indicator 98 is slidably received. A distance scale is printed or etched above and below the aperture 99 to provide an indication of distance in millimetres between the centres of two corrective lenses 35 in the test position of the first lens carrier housing 40 (the first test position) and the test position of the second lens carrier housing 70 (the second test position) respectively. As the adjustment knob 90 is rotated to adjust this distance, the indicator 98 slides within the aperture 99 so that the distance can be easily read by the user. In use of the portable apparatus 1 this distance scale can be used to measure the interpupillary distance of a person to be tested.

Figure 10:
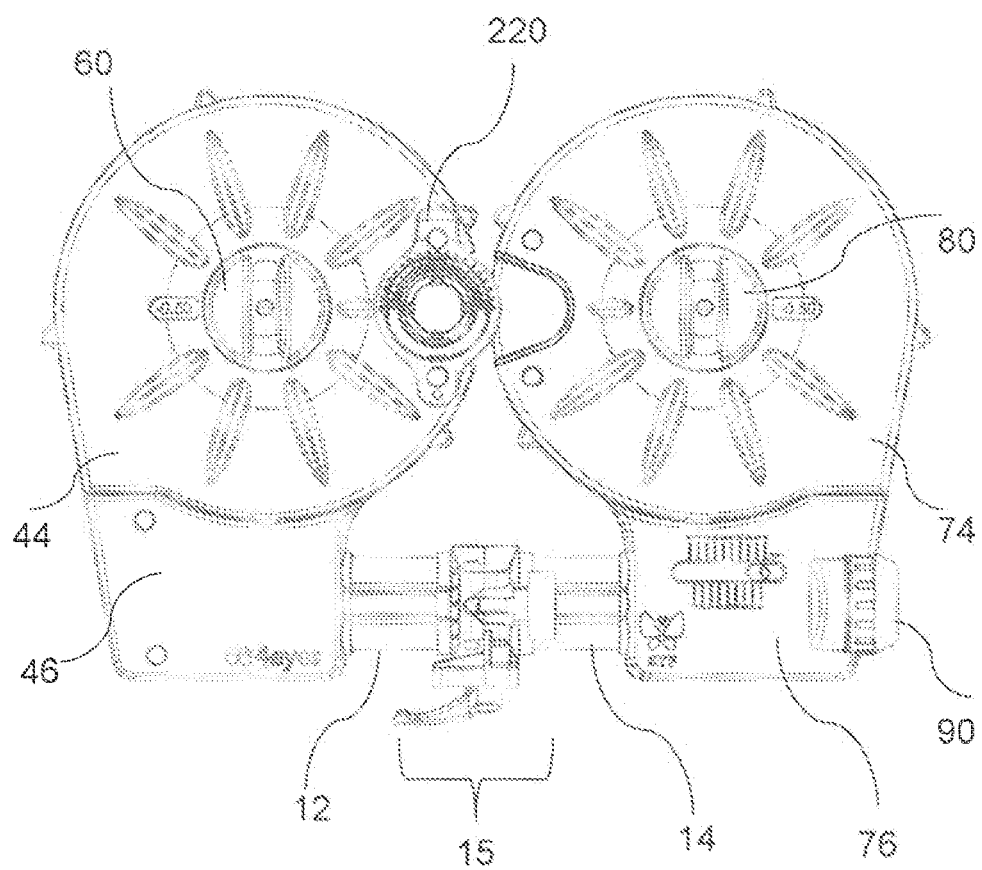
FIG. 10 is a front view of the portable apparatus with an additional astigmatism attachment.
Figure 11:
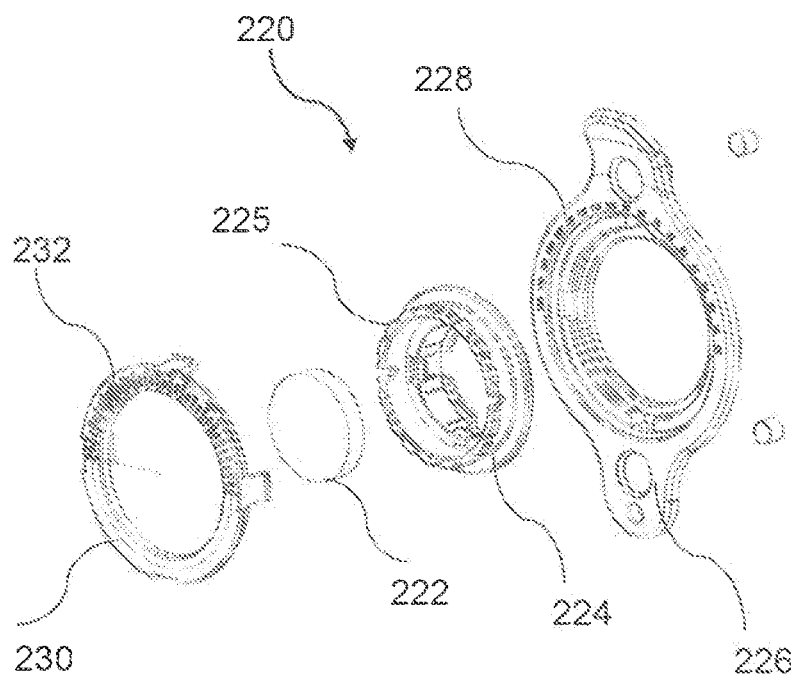
FIG. 11 is an exploded perspective view of the additional astigmatism attachment.

FIGS. 10 and 11 show an additional lens attachment in the form of astigmatic lens attachment 220 for use in testing for astigmatism in the eye of the person to be tested. The astigmatic lens attachment 220 has an astigmatic testing lens 222 fixedly housed in a rigid plastic annular housing 224. The rigid plastic annular housing 224 is itself rotatably received in a circular recess of a magnetic plastic outer housing 226. The annular housing 224 has a knurled annular flange 225 for ease of manual rotation by a user or operator of the portable apparatus 1. The outer housing 226 is constructed to magnetically attach to the front housings 44, 74 of the portable apparatus 1. In particular, as shown in FIG. 10, the astigmatic lens attachment 220 fits over the testing positions 56 of each of the first lens wheel 20 and the second lens wheel 30 so that astigmatism in the eyes of a person being tested can be determined. An annular cover 230 clips over the lens 222 onto the outer housing 226 to keep the annular housing 124 in place whilst exposing the knurled flange 225 for rotation by the operator of the portable apparatus 1. An upper half of the cover 230 has a plurality of measurement markings 232 printed or etched around the lens perimeter. An upper half of the outer housing 226 is marked with an angular scale 228 from 0 degrees to 180 degrees. The annular housing 224 together with the lens 222 are rotatable by an operator of the portable apparatus 1 relative to the outer housing 226 to carry out the test and measure an angle of astigmatism using the scale 228. Although not shown in the drawings, the additional lens attachment can also or alternatively be a further strength of corrective lens 35 so that additional lens powers can be tested. For example, the additional corrective lens can be of strength 0.25 that can be used in addition to the lenses of the lens carriers 20, 30 to provide a greater degree of precision in determining the prescription requirement of the person to be tested.

As seen in FIG. 1, and FIG. 2, the hinge assembly 15 includes a tripod mount 190 at a lower end thereof. The tripod mount 190 is adapted for mounting onto a standard camera tripod (not shown) so that the portable apparatus 1 can be held steady at a desired height at the test site. Whilst the tripod mount 190 is part of the rigid plastic hinge assembly 15 in this embodiment, it may alternatively form part of the base rails 12, 14.

Figure 12:
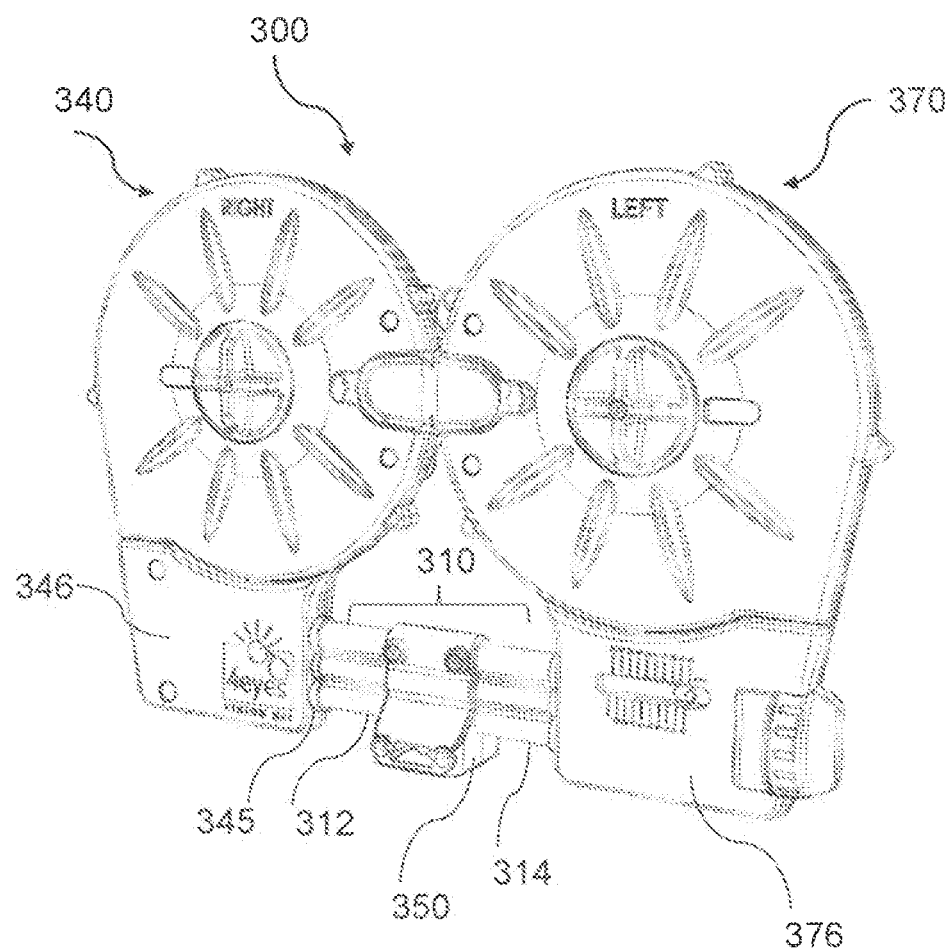
FIG. 12 is a front perspective view of a second embodiment of the portable apparatus.
Figure 13:
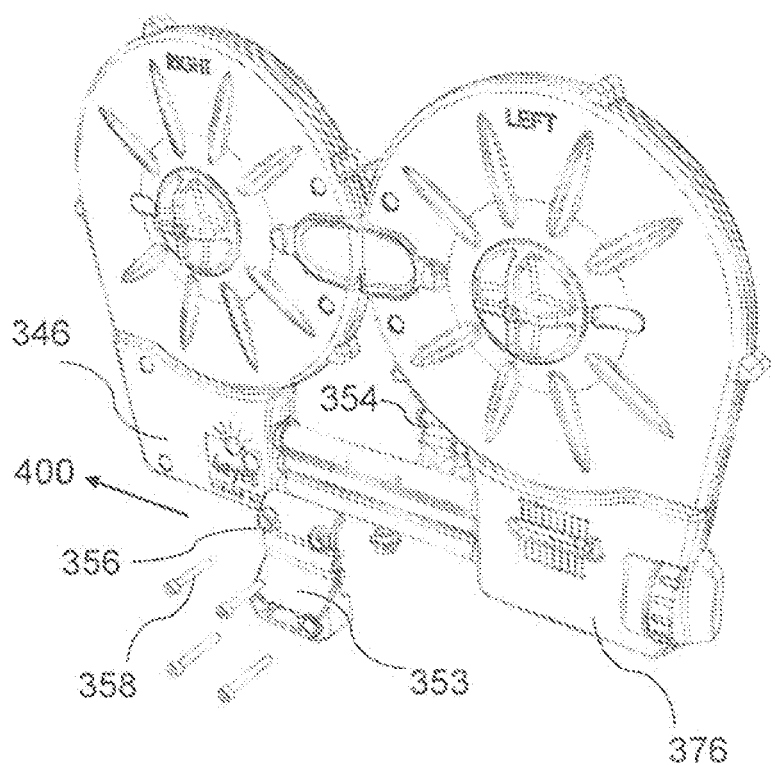
FIG. 13 is the front perspective view of FIG. 12 showing an exploded mounting bracket.
Figure 14:
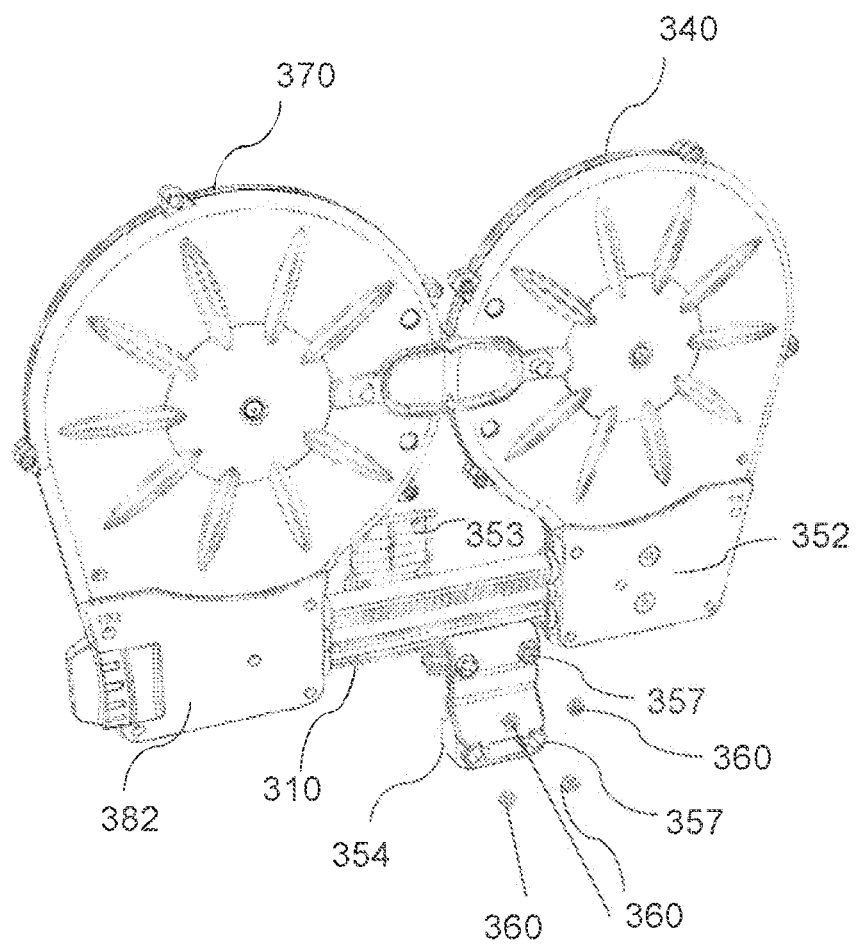
FIG. 14 is a rear perspective view of the embodiment of FIG. 12, showing an exploded mounting bracket.

A second embodiment of the portable apparatus 300 is shown in FIGS. 12 to 14. The portable apparatus 300 is identical to the portable apparatus 1 in almost all respects with the exception of the base rail 310. As with the portable apparatus 1, the base rail 310 includes a left side base rail portion 312 and a right side base rail portion 314. However, in the portable apparatus 300, the left side base rail portion 312 and the right side base rail portion 314 are integrally formed with one another. There is no central hinge attaching the base rail portions together. A mounting bracket 350 is instead assembled onto a middle portion of the base rail 310, via which the portable apparatus 300 may be mounted to a standard camera tripod (not shown). Accordingly, the portable apparatus 300 is not foldable. However, the first lens carrier housing 340 is detachable from the base rail portion 312 for reducing the size of the portable apparatus 300 for transport. More specifically, the first lens carrier housing 340 is translatable or slidable away from the middle portion of the left side base rail portion 312 in the direction of the arrow 400 shown in FIG. 13, and off the end of the base rail portion 312 to detach it from the remainder of the portable apparatus 300. The first lens carrier housing 340 can then be placed over the second lens carrier housing 370, as if in the folded configuration of the portable apparatus 1, for transportation. As with the portable apparatus 1, the flanges 345 of the lower front casing 346 and lower rear casing 352 are moulded to include contours in the vertical sides thereof that correspond to the ridges in the left side base rail portion 312 such that the base rail portion 312 can be received in the lower casing 346, 352 with a positive location fit in the vertical axis. When it is desired to assemble the portable apparatus 300, the left side base rail 312 is inserted into the lower casing 346, 352 to reassemble the portable apparatus 300. A stop element or flange (not shown) may be included on the left side base rail portion 312 to prevent the base rail portion 312 from being inserted too far into the lower casing 346, 352. It will be apparent to the skilled person that it is the first lens carrier housing 40 that is detachable from the base rail portion 312 as the second lens carrier housing includes the adjustment mechanism for measuring interpupillary distance. However, in a different embodiment, the adjustment mechanism could equally be present on the first lens carrier housing, in which case the second lens carrier housing would be detachable from the base rail portion 314.

The mounting bracket 350 comprises a front mounting bracket portion 353 and a rear mounting bracket portion 354. The front mounting bracket portion 353 has a rear face that contacts the base rail 310. The rear surface is contoured with a complementary profile to the ridged front face of the base rail 310 so that the front mounting bracket portion 352 can be positively located on the base rail 310 in the vertical axis. The rear mounting bracket portion 354 has a rear surface with a similarly complementary profile to the ridged rear face of the base rail 310 so that the rear mounting bracket portion 354 can be positively located on the base rail 310 in the vertical axis. Each of the front mounting bracket portion 353 and the rear mounting bracket portion 354 includes upper and lower fixing apertures 356, 357 in which bolts 358 can be received for attaching the mounting bracket 350 to the base rail 310. The bolts 358 are held in place via nuts 360. A lower portion of the mounting bracket 350 includes a tripod mount that is adapted for mounting onto a standard camera tripod (not shown).

It will be apparent to the skilled person that an embodiment of the apparatus may include both a foldable base rail as described in the first embodiment and a removable lens carrier housing as described in the second embodiment, without departing from the scope of the invention.

The operation of the portable apparatus 1, 300 will now be described.

The portable apparatus 1 is operated as follows. The portable apparatus 1 is transported to a test site in a folded configuration as shown in FIGS. 4 and 5. In the folded configuration, the locking pin 145 locks the left side hinge component 110 and the right side hinge component 130 together. The portable apparatus 1 is transported in a folded configuration. In the folded configuration, the locking pin 145 can be pivoted out of the open fronted channel 122a, 122b of the central hinge 15. The apparatus 1 is unfolded by rotating the right side hinge component 130 relative to the left side hinge component 110 to close the central hinge 15. In the closed position of the hinge 15, the locking pin 145 is re-pivoted into the open fronted channel 122a, 122b with its head located outside of the channel 122b. The locking pin 145 is screwed into the recessed portion 129 to lock the central hinge 15 in the closed position. If desired, the tripod mount 190 can be mounted to a standard camera tripod to raise the height of the portable apparatus 1 ready for use.

The portable apparatus 300 is operated as follows. The portable apparatus 300 is transported to a test site in a dismantled configuration, whereby the first lens carrier housing 340 is detached from the left side base rail portion 312. The apparatus 300 is assembled for use by firstly aligning the flanges 345 of the lower casing 346, 352 of the first lens carrier housing 340 with the contours/ridges at the end of the left side base rail portion 312. The left side base rail portion 312 is inserted into the lower casing 346, 352 until the stop member positively locates the left side base rail 312 relative to the first lens carrier housing 340 in the correct position, ready for use. The mounting bracket 350 on the base rail 310 can be mounted to a standard camera tripod to raise the height of the portable apparatus 300 ready for use.

The person to be tested sits or stands at the rear of the portable apparatus 1, 300. A corrective lens of the plurality of corrective lenses 35 is advanced into the test position at the cut-out segment 5 of the first lens carrier housing 40 by user rotation of the control knob 60. Positive location of the selected corrective lens 35 in the test position 56 takes place as the tip 49 of the ratcheted arm 48 engages in a detent notch 39 in the lens carrier 20. The strength of the corrective lens 35 in the test position 56 is easily read from the indicator 27.

The user or operator can test the clarity of vision of the right eye of the person to be tested using different corrective lenses 35 and the ability of the person to be tested to read standard wall charts of letters and numbers located at a set distance from the portable apparatus 1, 300 as is known in the art, to determine the refractive error and a suitable prescription for that eye. The blackout lens 37 is used in the second lens carrier 30 so that only the right eye is tested. The refractive error of the left eye of the person to be tested can be determined using the different strength corrective lenses 35 of the second lens carrier 30 and the blackout lens 37 of the first lens carrier 20. The distance between the pupils of the user to be tested is measured by adjusting the adjustment knob 90 to expand the width of the portable apparatus 1, 300 to thereby increase the distance between the testing positions 5, 7 of the first lens carrier 20 and the second lens carrier 30. The interpupillary distance is reached when the centres of both lenses 35 in the test positions aligns with the pupils of the eyes of the person to be tested. The interpupillary distance is read from the scale using the indicator 98. This measurement is used to size a spectacles frame for the person to be tested.

If necessary, the additional lens attachment in the form of a further corrective lens can be used to refine the prescription. An astigmatism attachment 220 can be attached over the test position of the first lens carrier housing 20 and the second lens carrier housing 30 to measure astigmatism in the eyes of the person to be tested. The astigmatic lens 222 can be rotated, via the knurled flange 225 of the annular housing 224, within the outer housing 226 by the operator to test different degrees of astigmatism.

Once a person's lens requirements and interpupillary distance are determined using the portable apparatus 1, 300, spectacles can be assembled using innovative spectacle frames (not described here) and pre-cut optical lenses.

The portable apparatus 1, 300 has several advantages. It is a robust testing apparatus that in one embodiment thereof, has a folding mechanism so that the whole apparatus can be packed compactly for transport. In another embodiment, it can be partially dismantled for compactness during transport. Both embodiments of the portable apparatus 1, 300 are unique in that they are inexpensive, robust, and portable. These characteristics ensure the portable apparatus can be used to service remote and developing communities. Its simplified design is intended to make it easy for untrained professionals to learn how to determine refractive error and thus choose the required spectacle lenses. It also measures interpupillary distance which is needed to size the spectacle frame. Another unique feature of the portable apparatus 1, 300 is the option of adding lenses with a magnetic attachment, to extend the range of lens strengths and to test for astigmatism. The innovative portable apparatus 1, 300 enables non-professionally trained people to determine refractive error in the field, remote from and without the need for an optometrist's office. This portable apparatus 1, 300 is predicted to achieve 85-90% of the accuracy obtained by a professional refractionist.

A simple training manual is provided which explains how the carrier is used. The operator learning the testing method is then given a theoretical and practical objective test of their skill with the portable apparatus 1, 300, and must accurately identify a series of test lens strengths, before prescribing and dispensing glasses to people. The portable testing apparatus 1, 300, tripod, vision charts and training manual are supplied in a hard case for transport.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A portable apparatus for determining refractive error in the human eye, the apparatus comprising an elongate base rail having a left side base rail portion and a right side base rail portion; a first lens carrier housing mounted on the left side base rail portion, a first lens carrier carrying a plurality of corrective lenses and being substantially housed within the first lens carrier housing so as to expose a corrective lens of the first lens carrier in a test position of the first lens carrier housing; a second lens carrier housing mounted on the right side base rail portion, a second lens carrier carrying a plurality of corrective lenses and being substantially housed within the second lens carrier housing so as to expose a corrective lens of the second lens carrier in a test position of the second lens carrier housing; a first user operable control adapted for moving the first lens carrier relative to the first lens carrier housing and a second user operable control adapted to move the second lens carrier relative to the second lens carrier housing, whereby the first user operable control and the second user operable control are each movable to select a corrective lens to be exposed in the test position of the respective carrier housing; and wherein the portable apparatus includes at least one of (a) the base rail is adapted to be foldable at a middle portion thereof and (b) one of the first lens carrier housing and the second lens carrier housing is detachable from the respective left side base rail portion or right side base rail portion.

2. The portable apparatus of claim 1, wherein the base rail is adapted to be foldable about a vertical axis so as to fold the portable apparatus in half.

3. The portable apparatus of claim 1, wherein one of the first lens carrier housing and the second lens carrier housing is selectively movable on the base rail relative to the other of the first lens carrier housing and the second lens carrier housing to adjust a distance between the first lens carrier housing and the second lens carrier housing.

4. The portable apparatus of claim 1, wherein the first lens carrier and the second lens carrier each comprise a disc, and wherein the plurality of corrective lenses of the respective lens carrier is arranged around a radially outer portion of the disc.

5. The portable apparatus of claim 1, wherein the first lens carrier and the second lens carrier are each rotatably mounted within the respective lens carrier housing.

6. The portable apparatus of claim 5, wherein the first user operable control is adapted to rotate the first lens carrier and the second user operable control is adapted to rotate the second lens carrier, to advance a corrective lens of the plurality of corrective lenses into the test position of the respective carrier housing.

7. The portable apparatus of claim 1, wherein the test position of the first lens carrier housing and the test position of the second lens carrier housing are disposed substantially adjacent one another.

8. The portable apparatus of claim 1, wherein the base rail includes a hinge disposed between and connecting the left side base rail portion and the right side base rail portion, wherein the apparatus is foldable about the hinge.

9. The portable apparatus of claim 3, further comprising a user operable adjustment mechanism, via which the one of the first lens carrier housing and the second lens carrier housing is selectively translatable on the base rail.

10. The portable apparatus of claim 1, wherein one of the first lens carrier housing and the second lens carrier housing is slidably mounted on the base rail for adjustable movement of the base rail relative to the one of the first and second lens carrier housings mounted thereon for varying a distance between the a test position of the first lens carrier housing and a test position of the second lens carrier housing.

11. The portable apparatus of claim 1, wherein the base rail includes an indicator of a distance between a centre of a corrective lens in the testing position of the first lens carrier housing and a centre of a corrective lens in the testing position of the second lens carrier housing.

12. The portable apparatus of a claim 1, wherein the first lens carrier housing and the second lens carrier housing each include a viewing window to an indicator of the lens power of the corrective lens in the test position.

13. The portable apparatus of claim 1, further including an additional lens attachment that is removably attachable to each of the first lens carrier housing and the second lens carrier housing.

14. The portable apparatus of claim 13, wherein the additional lens attachment includes a magnetic housing adapted for removable attachment to each of the first lens carrier housing and the second lens carrier housing.

15. The portable apparatus of claim 13, wherein the additional lens attachment includes an astigmatic testing lens.

16. The portable apparatus of claim 13, wherein the additional lens attachment includes a further corrective lens.

17. The portable apparatus of claim 1, wherein the base rail includes a mounting portion adapted for mounting the apparatus on a tripod or stand.

18. The portable testing apparatus of claim 17, wherein the mounting portion comprises a mounting bracket.

19. The portable testing apparatus of claim 17, wherein the mounting portion is a part of the hinge.

* * * * *